(12) United States Patent
Stevens et al.

(10) Patent No.: US 8,773,271 B1
(45) Date of Patent: Jul. 8, 2014

(54) APPARATUSES, SYSTEMS, AND METHODS FOR DETECTING AND REACTING TO EXPOSURE OF AN ELECTRONIC DEVICE TO MOISTURE

(71) Applicant: HzO, Inc., Draper, UT (US)

(72) Inventors: Blake Stevens, Morristown, NJ (US); Max Sorenson, Cottonwood Heights, UT (US)

(73) Assignee: HzO, Inc., Draper, UT (US)

( * ) Notice: Subject to any disclaimer, the term of this patent is extended or adjusted under 35 U.S.C. 154(b) by 0 days.

(21) Appl. No.: 14/150,534

(22) Filed: Jan. 8, 2014

Related U.S. Application Data

(60) Provisional application No. 61/750,328, filed on Jan. 8, 2013.

(51) Int. Cl.
*G08B 21/00* (2006.01)

(52) U.S. Cl.
USPC .......................................................... 340/604

(58) Field of Classification Search
USPC ........... 340/604, 605, 620, 618, 815.4; 361/1, 361/71
See application file for complete search history.

(56) References Cited

U.S. PATENT DOCUMENTS

| | | |
|---|---|---|
| 3,898,547 A | 8/1975 | Poole |
| 4,994,726 A | 2/1991 | Tamura et al. |
| 5,291,118 A | 3/1994 | Kojima |
| 5,865,635 A | 2/1999 | Hsiang et al. |
| 5,999,384 A | 12/1999 | Chen et al. |
| 6,061,261 A | 5/2000 | Chen et al. |
| 6,552,888 B2 | 4/2003 | Weinberger |
| 7,332,834 B2 | 2/2008 | Lee |
| 7,411,317 B2 | 8/2008 | Liu |
| 7,795,759 B2 | 9/2010 | DuBose et al. |
| 7,800,252 B2 | 9/2010 | DuBose et al. |
| 7,977,823 B2 | 7/2011 | DuBose et al. |

(Continued)

FOREIGN PATENT DOCUMENTS

| | | |
|---|---|---|
| JP | 09-107327 | 4/1997 |
| JP | 2003-115949 A | 4/2003 |

(Continued)

OTHER PUBLICATIONS

United States Patent and Trademark Office acting as the International Searching Authority, "International Search Report and Written Opinion," mailed Mar. 14, 2013, in PCT application No. PCT/US2013/020376.

(Continued)

*Primary Examiner* — Phung Nguyen
(74) *Attorney, Agent, or Firm* — Durham Jones & Pinegar Intellectual Property Law Group

(57) ABSTRACT

An electronic device includes a port for connecting the electronic device to other electronic devices and a moisture detector configured to detect an electrically conductive liquid in the first port. The moisture detector is configured to maintain a voltage on a first electrical contact of the port and to detect a short circuit between the first electrical contact and a second electrical contact of the port. The moisture detector determines that the electronic device has been exposed to an electrically conductive liquid if the monitor module detects the short circuit. The moisture detector may also put the electronic device into safe mode if it is exposed to an electrically conductive liquid.

30 Claims, 8 Drawing Sheets

(56) References Cited

U.S. PATENT DOCUMENTS

| | | |
|---|---|---|
| 7,978,447 B2 | 7/2011 | Baxter |
| 7,990,670 B2 * | 8/2011 | Chen ............................ 361/88 |
| 8,000,858 B2 | 8/2011 | Tonegawa et al. |
| 8,030,890 B2 | 10/2011 | Hyatt |
| 8,169,196 B2 | 5/2012 | Vantu et al. |
| 8,198,757 B2 | 6/2012 | Brink et al. |
| 8,368,350 B2 | 2/2013 | Iwanaga et al. |
| 8,374,729 B2 | 2/2013 | Chapel et al. |
| 8,519,566 B2 | 8/2013 | Recker et al. |
| 2002/0074970 A1 | 6/2002 | Kawashima |
| 2002/0097546 A1 | 7/2002 | Weinberger |
| 2002/0101695 A1 | 8/2002 | Saksa |
| 2002/0112945 A1 | 8/2002 | Lawson et al. |
| 2004/0130288 A1 | 7/2004 | Souther et al. |
| 2004/0257037 A1 | 12/2004 | Hartung et al. |
| 2005/0267698 A1 * | 12/2005 | Gordon ............................ 702/64 |
| 2006/0125434 A1 | 6/2006 | Frohne et al. |
| 2006/0181241 A1 | 8/2006 | Veselic |
| 2006/0208914 A1 * | 9/2006 | Liu et al. ...................... 340/620 |
| 2007/0038334 A1 | 2/2007 | Chou et al. |
| 2007/0254697 A1 | 11/2007 | Sugio et al. |
| 2008/0164768 A1 | 7/2008 | Litwack |
| 2008/0204218 A1 | 8/2008 | Tupman et al. |
| 2009/0001938 A1 | 1/2009 | Vantu et al. |
| 2009/0015372 A1 | 1/2009 | Kady |
| 2009/0122633 A1 | 5/2009 | Roewer |
| 2009/0263581 A1 | 10/2009 | Martin, III et al. |
| 2009/0263641 A1 | 10/2009 | Martin, III et al. |
| 2010/0033883 A1 * | 2/2010 | Simon ............................ 361/52 |
| 2010/0270860 A1 | 10/2010 | Kamaga |
| 2010/0302757 A1 | 12/2010 | Bennett, Jr. |
| 2010/0304091 A1 | 12/2010 | Wang |
| 2011/0104940 A1 | 5/2011 | Rabu et al. |
| 2011/0131003 A1 | 6/2011 | Tusvik |
| 2011/0147174 A1 | 6/2011 | Chuang |
| 2011/0208993 A1 | 8/2011 | Samoilova et al. |
| 2011/0262740 A1 | 10/2011 | Martin, III et al. |
| 2011/0264398 A1 | 10/2011 | Niewczas et al. |
| 2012/0194952 A1 | 8/2012 | Crucs |
| 2013/0174410 A1 | 7/2013 | Stevens et al. |
| 2013/0176691 A1 | 7/2013 | Stevens et al. |
| 2013/0176700 A1 | 7/2013 | Stevens et al. |
| 2013/0182360 A1 * | 7/2013 | Stevens et al. ............... 361/71 |
| 2013/0286567 A1 | 10/2013 | Sorenson et al. |
| 2013/0295782 A1 | 11/2013 | Goel |
| 2013/0335898 A1 | 12/2013 | Stevens et al. |

FOREIGN PATENT DOCUMENTS

| | | |
|---|---|---|
| JP | 2004-235724 A | 8/2004 |
| JP | 2004-297629 A | 10/2004 |
| JP | 2006-277129 A | 10/2006 |
| JP | 2010-035036 A | 12/2010 |
| JP | 2011-171894 A | 9/2011 |
| WO | 2006028030 A1 | 3/2006 |

OTHER PUBLICATIONS

United States Patent and Trademark Office, Acting as The International Searching Authority, "International Search Report and Written Opinion," mailed May 2, 2014, in related PCT application No. PCT/US2014/010720.

* cited by examiner

APPARATUSES, SYSTEMS, AND METHODS FOR DETECTING AND REACTING TO EXPOSURE OF AN ELECTRONIC DEVICE TO MOISTURE

CROSS-REFERENCE TO RELATED APPLICATION

A claim for the benefit of priority is hereby made pursuant to 35 U.S.C. §119(e) to the Jan. 8, 2013 filing date of U.S. Provisional Patent Application No. 61/750,328, titled APPARATUSES, SYSTEMS, AND METHODS FOR DETECTING AND REACTING TO EXPOSURE OF AN ELECTRONIC DEVICE TO MOISTURE. The entire disclosure of which is hereby incorporated herein.

TECHNICAL FIELD

This disclosure relates generally to methods and systems for detecting exposure of an electronic device to moisture. More particularly, this disclosure relates to approaches for detecting the presence of electrically conductive moisture at one or more electrically conductive contacts of an electronic device, including the contacts of ports of the electronic device.

BACKGROUND OF RELATED ART

The durability of electronic devices is a major concern to consumers. Protective cases for cellular telephones, tablet computers, portable media players, laptop computers, and other electronic devices are in high demand. Most of these cases provide protection from scratches and other physical damage; very few cases provide protection against water damage. Protective cases that provide protection against water damage do so by ensuring that the electronic device is not exposed to water, and generally encase or envelop the entire electronic device. As a result, waterproof cases tend to be somewhat bulky or large and limit access to the electronic device.

Some companies, such as HzO, Inc., take a different approach to protecting electronic devices from water. HzO's approach employs the application of a thin film, or protective coating, to circuitry and/or components inside of an electronic device. This protective coating protects the electronic device from water and other types of moisture without requiring a bulky external protective case. The moisture-resistant coatings that have been developed by HzO protect electronic devices from a variety of different types of incidental or accidental exposure to moisture, including high humidity, rain, spilled drinks, the washing machine or even if the device is dropped in water.

While protective coatings like those developed by HzO may protect the interior of an electronic device, the ports of the electronic device, including ports that enable charging of the battery of the electronic device and/or enable the electronic device to electrically couple to and/or communicate with other devices (e.g., computers, peripheral devices, etc.) are typically still exposed to moisture, as it is necessary to establish electrical contact with the electrically conductive features (e.g., pins, leads, other electrical contacts, etc.) of the ports for the ports to serve their intended use(s).

Being able to determine whether the ports or other electrical contacts of an electronic device are exposed to moisture may allow for greater protection of the electronic device. While certain electronic devices on the market contain moisture sensors, many of these sensors are one-time use sensors that irreversibly react to the presence of moisture. For example, a portable consumer electronic device may include one or more internal water damage sensors, which are often embodied as stickers, that enable a service technician to determine whether the device has been exposed to moisture and, thus, whether the product warranty for the device has been voided. The sensor does not, however, terminate operation of any portion of the electronic device upon exposure of the electronic device to moisture, communicate with the electronic device or provide an individual who uses the electronic device with a warning or other indicator that the electronic device has been exposed to moisture. Nor can the sensor be reset after exposure to moisture.

SUMMARY

An electronic device according to this disclosure includes a sensor that can report when a port or another electrical contact of the electronic device has been exposed to electrically conductive moisture, or liquid. A moisture detector may communicate with a moisture detection circuit that includes the port or another set of electrical contacts. The moisture detector may include a monitor module and a sensor module.

The monitor module may be configured to monitor one or more properties of the moisture detection circuit (e.g., electrical properties, mechanical properties, optical properties, magnetic effects, etc.). In a specific embodiment, the monitor module may be configured to maintain a voltage on a first electrical contact and to detect a short circuit of the first electrical contact to a second electrical contact. The moisture detection circuit (e.g., the port or other electrical contacts thereof) may comprise a first node with a first voltage and a second node with a second voltage, which is different from the first voltage.

The moisture detector may also include a sensor module configured to determine that the moisture detection circuit is exposed to an electrically conductive liquid in response to the properties of the moisture detection circuit corresponding to reference properties characteristic of exposure to an electrically conductive liquid. Continuing with the specific embodiment provided above, in which the monitor module may detect a short circuit, the sensor module may be configured, in response to the monitor module detecting the short circuit, to determine that the port or other group of electrical contacts has been exposed to an electrically conductive liquid.

Further disclosed is a method for determining exposure of a port or other electrical contacts to an electrically conductive liquid. The method may include providing a first voltage at a first electrical contact of a plurality of electrical contacts (e.g., a first contact of a port, etc.) of an electronic device while the port is in an unconnected state. The method may also include monitoring electrical activity at one or more of the electrical contacts while the port is in the unconnected state. In addition, the method may include sensing an electrical activity pattern at one or more of the electrical contacts, which electrical activity pattern is characteristic of a short circuit caused by an electrically conductive liquid. The method may further include determining exposure to an electrically conductive liquid in response to sensing an electrical activity pattern characteristic of a short circuit caused by the electrically conductive liquid.

Other aspects, as well as the features and advantages of various aspects, of the disclosed subject matter will become apparent to those of ordinary skill in the art through consideration of the ensuing description, the accompanying figures, and the appended claims.

DETAILED DESCRIPTION

Figure 1:
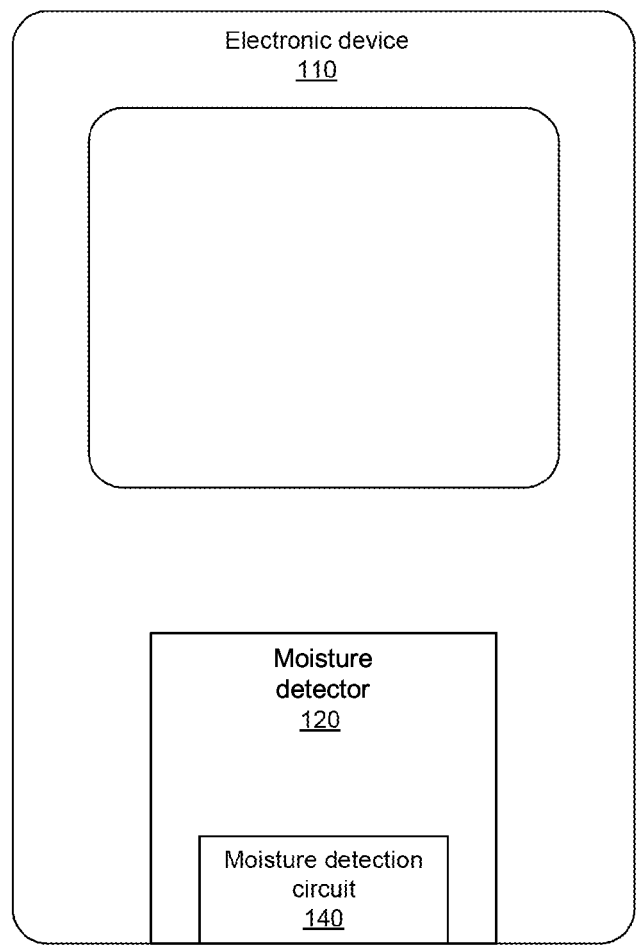
FIG. 1 is a schematic representation of an embodiment of an electronic device including a moisture detector.

FIG. 1 illustrates an embodiment of an electronic device 110 comprising a moisture detector 120 and a moisture detection circuit 140. The moisture detector 120 and moisture detection circuit 140 cooperate to determine whether the electronic device 110 has been exposed to an electrically conductive liquid. An electrically conductive liquid refers to those liquids that are electrical conductors containing movable electric charges that can move relatively freely through the liquid. For example, the electrically conductive liquid may be tap water, rain water, salt water, juice, or other liquids having movable electric charges. Generally, exposing an unprotected electronic device 110 to an electrically conductive liquid can cause damage to the electronic components within. The electronic device 110 may be exposed to the electrically conductive liquid by being submerged, by having an electrically conductive liquid in the air condense on or in the electronic device 110, or in other ways.

The moisture detector 120 is configured to detect when the electronic device 110 is exposed to an electrically conductive liquid. The moisture detector 120 may take steps to protect the electronic device 110 in response to determining that the electronic device 110 has been exposed to an electrically conductive liquid via moisture detection circuit 140. The moisture detector 120 may help protect the electronic device 110 from damage when the electronic device 110 is exposed to conductive liquids.

The electronic device 110 may be capable of executing and storing instructions. A few non-limiting examples of electronic devices 110 include cellular telephones, tablet computers, portable media players, wearable electronic devices, laptop computers, digital readers, and other consumer electronic devices. Teachings of this disclosure are also applicable to a wide variety of other types of electronic devices, including industrial electronics, electronics in vehicles, medical devices, etc. A typical electronic device 110 can be severely damaged if exposed to an electrically conductive liquid.

The moisture detector 120 may include a moisture detection circuit 140. The moisture detection circuit 140 includes one or more electrical components that react when exposed to an electrically conductive liquid. The moisture detector 120 may monitor the moisture detection circuit 140 for changes in electrical, mechanical, optical and magnetic properties that are characteristic of exposure to an electrically conductive liquid.

In one embodiment, the moisture detection circuit 140 includes a first node with a first voltage, and a second node with a second voltage that is different from the first voltage. For example, the first node may have a voltage of 5 Volts, and the second node may be at ground potential (0 Volts). The moisture detector 120 may monitor the properties of the moisture detection circuit 140 and determine that the moisture detection circuit 140 has been exposed to an electrically conductive liquid in response to the properties of the moisture detection circuit 140 corresponding to changes in first node and second node reference properties characteristic of exposure to an electrically conductive liquid.

For example, exposure to an electrically conductive liquid may create a short circuit between the first node and the second node. As used herein, a short circuit refers to an abnormal connection of two nodes of an electric circuit creating a low impedance path, such as a connection made by water. The short circuit may alter one or more properties of the moisture detection circuit 140. The voltages at one or more nodes may change in response to the short circuit. The amount of current flowing in the moisture detection circuit 140 may change in response to the short circuit. The measured resistance of the moisture detection circuit 140 may change in response to the short circuit. The measured frequency of the moisture detection circuit 140 may change in response to the short circuit. Those of skill in the art will appreciate the ways in which a short circuit may alter properties of a circuit.

The moisture detector 120 may store one or more reference properties characteristic of exposure to an electrically conductive liquid. For example, the moisture detector 120 may store a set of reference properties that are derived from a model of an electrically conductive liquid forming a short circuit between the first node and the second node. The moisture detector 120 may compare the measured properties of the moisture detection circuit 140 with the reference properties derived from the model. The moisture detector 120 may determine that the electronic device 110 has been exposed to an electrically conductive liquid in response to the measured properties corresponding to the reference properties. As used herein, values may correspond to one another if they are within an acceptable range of one another. For example, a reference current value may be 200 mA. The moisture detector 120 may determine that any measured current value within 10% of the reference current value corresponds to the reference current value. The particular margin of error may depend upon the difference between the current value under normal conditions and the current value when exposed to an electrically conductive liquid.

Figure 2:
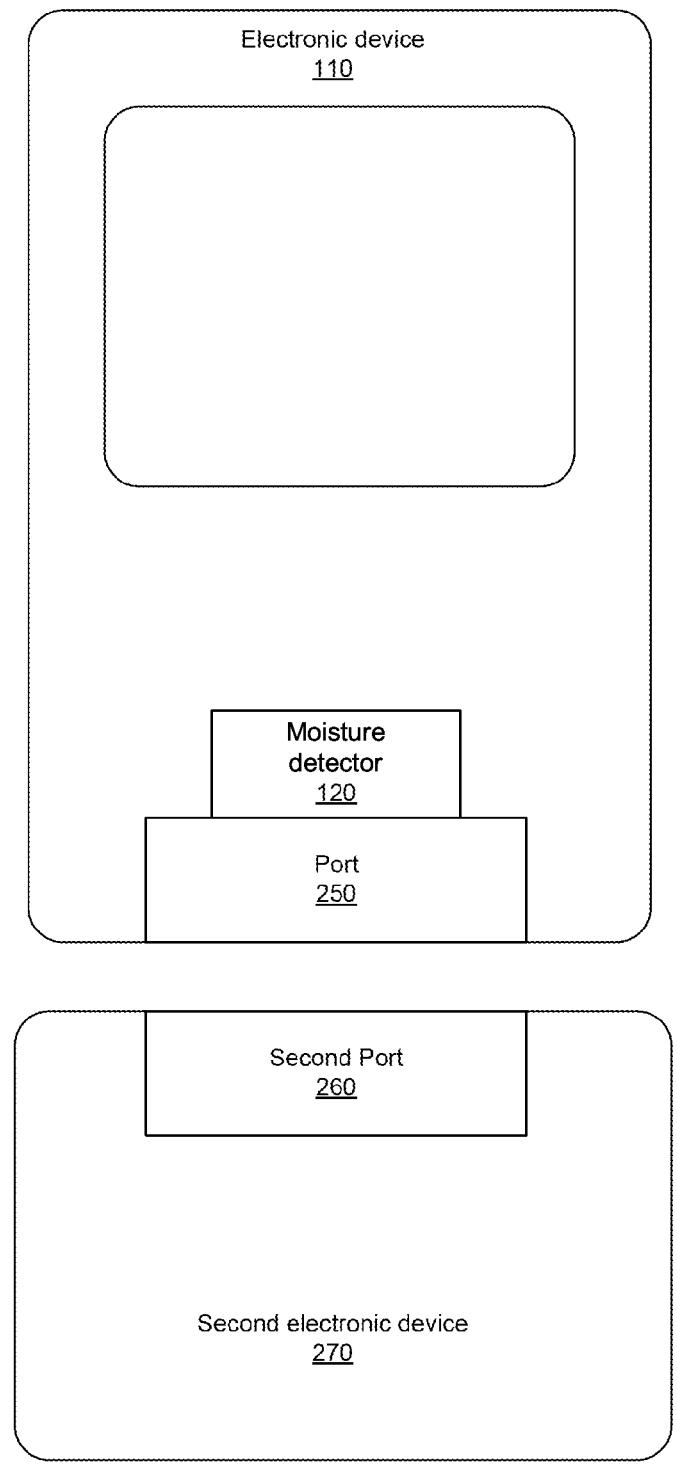
FIG. 2 is a schematic representation of an embodiment of an electronic device including a moisture detector and a port configured to enable communication with another electronic device.

FIG. 2 illustrates one embodiment of an electronic device 110 comprising a moisture detector 120 and a port 250, and a second electronic device 270 with a second port 260. The second electronic device 270 is an electronic device capable of sharing data and/or electrical power with the electronic device 110. Typical second electronic devices 270 include desktop computers, laptop computers, stereos, charging stations, and others.

The second electronic device 270 typically includes a second port 260 that allows the second electronic device 270 to connect to the electronic device 110 through the port 250. The second electronic device 270 and the electronic device 110 may directly connect via the port 250 and the second port 260. For example, the second port 260 may be a docking port and the port 250 may be a dock connector for the electronic device 110. The second electronic device 270 may indirectly connect to the electronic device 110. For example, a cable may connect the second port 260 and the port 250, allowing a transfer of data and/or power.

The port 250 may be a standard port such as a Universal Serial Bus (USB) port. The port 250 may be a proprietary port. In other embodiments, the port 250 may have a proprietary configuration but communicate using a standard peripheral interface. For example, an iPhone® has a proprietary 30-pin connector, but can connect to a second port 260 that is a USB port. Other variations of ports 250, and the corresponding second ports 260, are within the scope of this invention. The port 250 may be referred to as a first port to distinguish it from the second port 260 of the second electronic device 270.

In certain embodiments, the moisture detector 120 implements the moisture detection circuit 140 (FIG. 1) using the port 250. In such embodiments, the port 250 may comprise the moisture detection circuit 140. The moisture detector 120 may be realized in existing hardware of an electronic device 110 such that additional hardware to implement the moisture detection circuit 140 is unnecessary. For example, the moisture detector 120 may be realized at least in part on a controller for the port 250.

Figure 3:
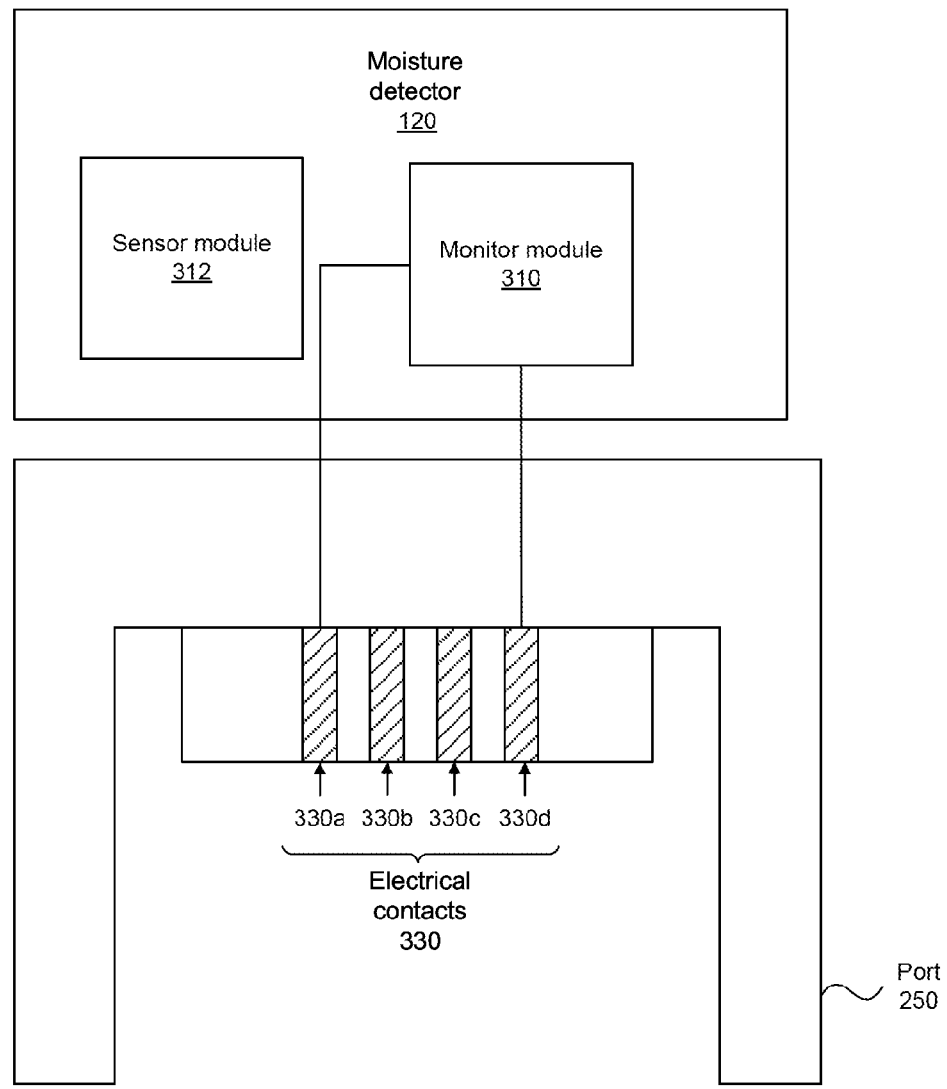
FIG. 3 is a schematic diagram illustrating an embodiment of a moisture detection circuit that includes a port of an electronic device.

FIG. 3 illustrates one embodiment of a moisture detector 120 comprising a sensor module 312 and a monitor module 310. The port 250 of the moisture detector 120 may include a plurality of electrical contacts 330, also commonly referred to as pins 330a, 330b, 330c, 330d. Electrical signals on the electrical contacts 330 may transfer power and/or data through the port 250. The number of pins may vary based on the particular type of port; for example, a USB 2.0 port may include a ground pin, a 5 Volt pin for providing and/or receiving power, and two data line pins (D+ and D−) for communicating data.

In the depicted embodiment, the moisture detector 120 is associated with the port 250 and detects an electrically conductive liquid in the port 250. The moisture detector 120 includes a monitor module 310 configured to maintain a voltage on at least one electrical contact 330. For example, the monitor module 310 may maintain 5 Volts on a first electrical contact 330a. The monitor module 310 may be configured to detect a short circuit between the first electrical contact 330a and a second electrical contact, such as electrical contact 330d. In one embodiment, the monitor module 310 places 5 Volts on the first electrical contact 330a used to transfer power, and monitors for a short circuit between the first electrical contact 330a and the second electrical contact 330d representing 0 Volts, or ground. The designations "first electrical contact" and "second electrical contact" are not used to refer to any particular electrical contact of the port 250; rather, the designations "first" and "second" are used to emphasize that the first electrical contact and the second electrical contact are different electrical contacts within the port 250. The sensor module 312 may be configured to determine that the electronic device 110 (FIGS. 1 and 2) is exposed to an electrically conductive liquid in response to the monitor module 310 detecting the short circuit.

In certain embodiments, the monitor module 310 may also monitor and determine the connection state of the port 250. The monitor module 310 may inform the sensor module 312 as to whether the port 250 is in an unconnected state or a connected state. The sensor module 312 may be configured to determine that the electronic device 110 is exposed to an electrically conductive liquid if the monitor module 310 detects that the port 250 is in an unconnected state, and that there is a short circuit. Such an embodiment may allow the sensor module 312 to distinguish between a short circuit caused by an electrically conductive liquid and a short circuit caused by a faulty cable or second electronic device 270. The sensor module 312 may assume that any short circuit detected while the port 250 is connected to a second electronic device 270 is due to a failure in the second electronic device 270 or connecting cable.

The sensor module 312 may use one or more exposure models that include reference properties to determine whether or not the electronic device 110 (FIGS. 1 and 2) has been exposed to an electrically conductive liquid. For example, the sensor module 312 may have an exposure model that includes reference properties characteristic of exposure to tap water, and a separate exposure model including reference properties characteristic of exposure to salt water. In such embodiments, the sensor module 312 may additionally make intelligent assumptions about the type of electrically conductive liquid to which the electrical device 110 has been exposed in addition to determining whether or not exposure to an electrically conductive liquid has occurred.

In certain embodiments, the exposure model is created using an artificial neural network (ANN), a look-up table, artificial intelligence, or another learning algorithm or system. An ANN is a network of processors that processes information using a connectionist approach. The ANN is an adaptive system that can model complex relationships and find patterns in data sets. The ANN may be provided with multiple data sets containing data generated by exposing a moisture detection circuit 140 (FIG. 1) to conductive liquids. The data sets may contain measured properties of the moisture detection circuit 140 exposed to the electrically conductive liquid. The moisture detection circuit 140 used to generate the data sets is preferably identical or substantially similar in architecture to the moisture detection circuits 140 that will be used in the electronic devices 110.

The ANN may use any appropriate learning paradigm (including supervised, unsupervised, and reinforcement learning) and any appropriate learning algorithm (such as evolutionary methods, simulated annealing, or others) to generate the exposure model. The sensor module 312 may be configured to receive updated exposure models from a remote server storing and distributing one or more exposure models. Similarly, the sensor module 312 may be configured to send the measured properties measured on the electronic device 110 to the remote server. An ANN may collect the measured properties from a plurality of electronic devices 110 and continue to refine the exposure model using these measured properties.

Figure 4:
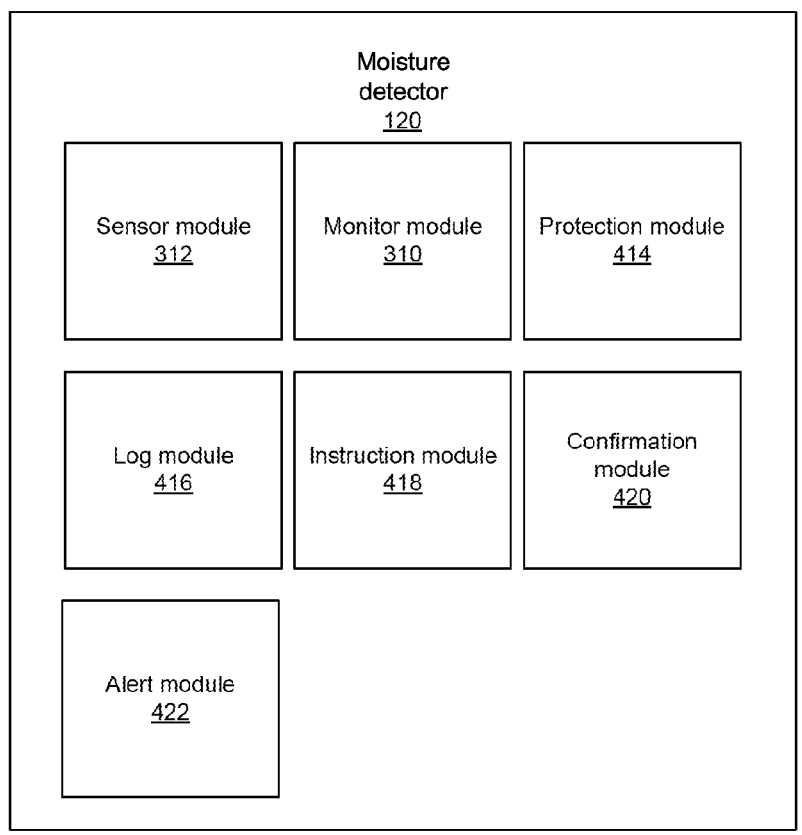
FIG. 4 is a block diagram illustrating an embodiment of a moisture detector.

FIG. 4 illustrates another embodiment of a moisture detector 120. The moisture detector 120 may include a sensor module 312 and a monitor module 310 as described above. The moisture detector 120 may also include a protection module 414. The protection module 414 may be configured to place the electronic device 110 in a safe mode in response to the sensor module 312 determining that the electronic device 110 is exposed to an electrically conductive liquid. As used herein, a safe mode refers to a mode of operation where one or more hardware elements of the electronic device 110 are disabled. For example, the protection module 414 may disable a Bluetooth module, a global positioning system (GPS) module, and other modules in response to the protection module 414 putting the electronic device 110 in safe mode. While the electronic device 110 typically has reduced functionality in safe mode, the possibility of permanent damage due to exposure to the electrically conductive liquid may be reduced.

The protection module 414 may initially power off the electronic device 110 in response to the sensor module 312 determining that the electronic device 110 is exposed to an electrically conductive liquid. The protection module 414 may then restart the electronic device 110 in safe mode. In one embodiment, the protection module 414 automatically restarts the electronic device 110 in safe mode. In another embodiment, the protection module 414 leaves the electronic device 110 off and restarts the electronic device 110 in safe mode in response to the user powering on the electronic device 110. The protection module 414 may ensure that, upon the first restart after powering off in response to an electrically conductive liquid, the electronic device 110 is started in safe mode.

The protection module 414 may also run one or more diagnostic tests on the electronic device 110 after the sensor module 312 determines that the electronic device 110 has been exposed to an electrically conductive liquid. The protection module 414 may continue to start the electronic device 110 in safe mode in response to one or more components of the electronic device 110 failing the diagnostic tests. The diagnostic tests may include tests to determine the integrity of software and hardware on the electronic device 110. The diagnostic test may determine that one or more hardware components of the electronic device 110 have failed. The protection module 414 may prevent critical and non-critical components that fail the diagnostic test from starting.

The protection module 414 may terminate communication between a power supply of the electronic device 110 and at least some of electronic components of the electronic device 110. In one embodiment, the protection module 414 terminates communication between the power supply of the electronic device 110 and all electronic components other than those of the moisture detector 120. In embodiments where the moisture detector 120 is distributed across multiple electronic components, the protection module 414 may allow communication between the power supply and only those electronic components involved in executing the moisture detector 120.

In certain embodiments, the protection module 414 may control a switch for controlling communication between the power supply and one or more electronic components of the electronic device 110. The switch may have a normal position which provides power to all electronic components of the electronic device 110. The switch may also have a response position that terminates communication of power between the power supply and the electronic components of the electronic device 110. The protection module 414 may control power distribution by controlling the switch.

In other embodiments, the protection module 414 sends one or more messages to control power distribution within the electronic device 110. For example, the protection module 414 may power off certain electronic components by sending messages to a motherboard, bus controller, or other electronic component that manages the distribution of power in the electronic device 110. The protection module 414 may command on and command off electronic components of the electronic device 110 by sending appropriate messages to electronic components involved in power distribution.

The moisture detector 120 may also include a log module 416. The log module 416 may be configured to log each instance of the sensor module 312 determining that the electronic device 110 is exposed to the electrically conductive liquid. The log module 416 may create a log entry that comprises the properties that caused the sensor module 312 to determine that the electronic device 110 was exposed to an electrically conductive liquid. For example, the log module 416 may record voltage and/or current readings at one or more electrical contacts 330 of the port 250 (FIG. 3) for a relevant time period leading up to the determination by the sensor module 312. In certain embodiments, the log entries may be accessible by an authorized third-party. Such an embodiment may allow the exposure model, used to determine whether or not the electronic device 110 has been exposed, to be further refined. Allowing access to the log entries may also enable service personnel or an authorized third-party to determine the number of times the electronic device 110 has been exposed to an electrically conductive liquid. Such information may be relevant, for example, to determining warranty information or whether a protective coating needs to be re-applied to the electronic device 110.

The moisture detector 120 may also include an instruction module 418 that is configured to provide the user with one or more instructions for treating the electronic device 110 following exposure to an electrically conductive liquid. The instruction module 418 may display the instructions on a display of the electronic device 110. The instruction module 418 may send the instructions to an email address specified by the user. The instructions may instruct the user on what to do to reduce the possibility of damage to the electronic device 110. For example, the instructions may specify allowing the electronic device 110 to dry for a period of time before attempting to power on the electronic device 110. The instructions may direct the user to use compressed air to dry the electronic device 110, and to place the electronic device 110 in a desiccant.

In certain embodiments, the instruction module 418 may provide different instructions based on the type of conductive liquid to which the electronic device 110 has been exposed. As described above, the sensor module 312 may use multiple exposure models that allow the sensor module 312 to determine the type of conductive liquid to which the electronic device 110 has been exposed. The sensor module 312 may inform the instruction module 418 as to the type of conductive liquid to which the electronic device 110 was exposed. The instruction module 418 may tailor the instructions accordingly. For example, if the electronic device 110 was exposed to salt water, there is a risk that even after the water is removed the salt residue will cause electrical problems with the electronic device 110. The instruction module 418 may instruct the user to rinse the electronic device 110 in distilled water and/or tap water immediately after exposure to the salt water as part of the recovery process.

The moisture detector 120 may also include a confirmation module 420 that requests user confirmation that the electronic device 110 was exposed to an electrically conductive liquid. The confirmation module 420 may display the request for confirmation on the display of the electronic device 110, may generate an audio request for confirmation, or otherwise request user input. The confirmation module 420 may request the confirmation before the protection module 414 initiates one or more protection protocols; the confirmation module 420 may request the confirmation after the protection module 414 initiates protection protocols. The moisture detector 120 may abort the protection protocols in response to the user indicating that the electronic device 110 was not exposed to an electrically conductive liquid. The log module 416 may still log the event, and may further note in the entry that the user indicated that the electronic device 110 had not been exposed to an electrically conductive liquid. Log entries of false positives may be used to further refine the exposure model and may be used to modify a warranty model associated with use of the electronic device 110. Log entries of false positives followed by damage to a device may adversely impact warranty coverage for the electronic device 110.

The moisture detector 120 may also include an alert module 422 that generates an alert indicating that the electronic device 110 has been exposed to an electrically conductive liquid. The alert module 422 may generate an alarm perceivable by the user of the electronic device 110. The alert module 422 may, for example, generate an audible alarm, a visual alarm, a vibrating alarm, or the like. The alert module 422 may cause a display to visually indicate to the user that the electronic device 110 has been exposed to an electrically conductive liquid. For example, the alert module 422 may generate a message causing a visual indicator to appear on the display panel of the electronic device 110. The message may be a text-based message. The alert module 422 may also use additional visual indicators such as a flashing light. The alert module 422 may also use a combination of perceivable alerts such as an audible alarm and a text-based message.

The alert module 422 may be configured to generate and transmit a message to a remote monitoring service in response to the electronic device 110 being exposed to an electrically conductive liquid. The alert module 422 may use a cellular network, a wireless Internet network, or other suitable communications network to send the message. The alert module 422 may be configured to use one or more communications elements of the electronic device 110 to communicate the message. The message may include data generated by the log module 416 concerning the exposure to an electrically conductive liquid. The remote monitoring service may be the cellular phone provider, a mobile services provider, a warranty fulfillment provider, or other entity. The remote monitoring service may also be an employer of the user providing the electronic device 110. The alert module 422 may generate and transmit the message to multiple remote monitoring services.

The alert module 422 may also be configured to provide a user interface through which it may display images and receive inputs. In such embodiments, the alert module 422 may execute at least in part as an application on the electronic device 110. The alert module 422 may launch in response to the electronic device 110 being exposed to the electrically conductive liquid. The alert module 422 may provide a message concerning waterproofing features of the electronic device 110, such as the last time a water-resistant coating was applied to components of the electronic device 110. The alert module 422 may, in certain embodiments, provide warranty information, repair information, advertisements related to mitigating the potential damage caused by exposure of the electronic device 110 to moisture, and other moisture-related information.

Figure 5:
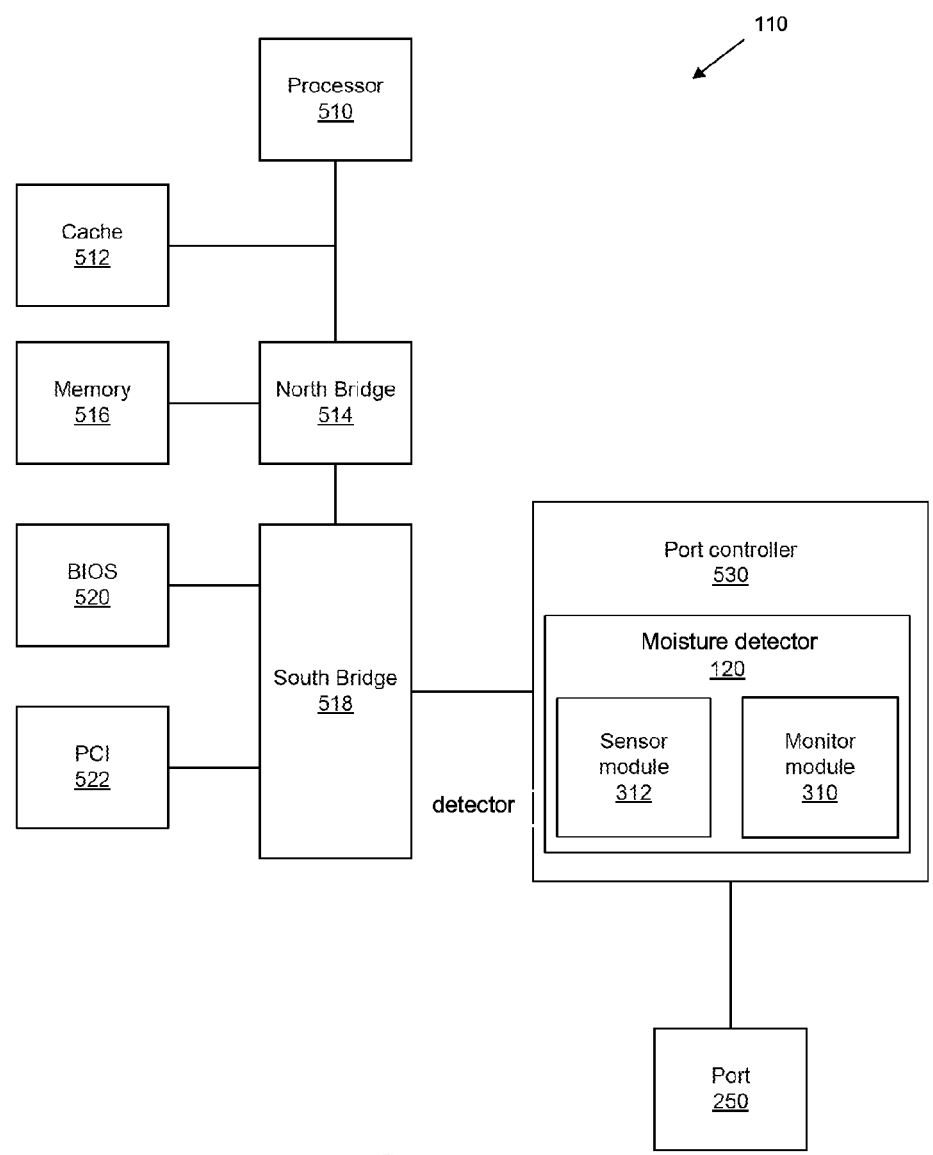
FIG. 5 is a block diagram illustrating an embodiment of a computing system including a moisture detector and a port controller.

FIG. 5 illustrates one embodiment of illustrative electronic components of an electronic device 110. The electronic device 110 may include a processor 510, a cache 512, a north bridge 514, memory 516, south bridge 518, basic input output system (BIOS) 520, Peripheral Controller Interface (PCI) 522, port controller 530, and a port 250. The system may include more, fewer, or different components than those shown in FIG. 5; for example, a system may include a serial AT attachment (SATA) controller, network interface cards (NICs), or other components. The architecture may also vary based on the type of electronic device; for example, a laptop and a smart phone may have different architectures and components.

The processor 510 executes a series of stored instructions for the system. Instructions and other data are stored in memory 516. The memory 516 may be dynamic random access memory (DRAM), static random access memory (SRAM), or other suitable memory. The processor 510 may use a fast cache 512 to reduce the time necessary to access frequently-used data instructions stored in memory 516. The north bridge 514 is a component for handling communications between the processor 510, memory 516, and the south bridge 518. The north bridge 514 may handle communications from other components as well, such as a video card.

The south bridge 518 provides input/output (I/O) functionality for the system and allows the system to make use of various additional components. The south bridge 518 may, for example, handle the basic input output system (BIOS) 520, PCI 522, and a port controller 530. The south bridge 518 may provide additional functionality not shown in FIG. 5 such as direct memory access (DMA), Ethernet connectivity, and others.

In one embodiment, the port 250 is a USB port. The port 250 may allow power and/or data to be transferred to and from the electronic device 110. The port 250 may be an upstream USB port receptacle or a downstream USB port receptacle. The port 250 may be configured to have a standard USB receptacle such as a Type A or Micro A-B receptacle.

The port controller 530 provides the necessary hardware and software/firmware to provide USB connectivity for the electronic device 110. In certain embodiments, the port controller 530 is integrated into the south bridge 518. In other embodiments, the port controller 530 is a separate chip connected to the south bridge 518 by a communications connection. The port controller 530 manages communications to and from the port 250 that can connect to various USB devices. The moisture detector 120 may be implemented, in whole or in part, as part of the port controller 530. The monitor module 310 and sensor module 312 may comprise firmware on the port controller 530.

Of course, the stated functions of the north bridge 514 and the south bridge 518 could be flipped.

The electronic components and circuitry may be provided with a water-resistant coating that increases the ability of the electronic components and circuitry to resist water damage and increases the likelihood that the electronic device 110 will continue to function properly following exposure to an electrically conductive liquid. The water-resistant coating may be applied to electronic components and circuitry without negatively impacting the normal operations of the electronic component. The water-resistant coating may cover all or part of the exterior of the electronic device 110, all or part of the internal surfaces of the electronic device 110, and one or more of the electronic components or circuitry of the electronic device 110. In certain embodiments, at least the electronic components associated with the moisture detector 120 are treated with the water-resistant coating. Where the moisture detector 120 uses a port 250 as a moisture detection circuit 140, at least some of the electrical contacts 330 (FIG. 3) may be left untreated in order to allow detection of conductive liquids.

In one embodiment, the water-resistant coating is a nanotechnology coating such as WaterBlock™ by HzO, Inc.

The moisture detector 120 in such an embodiment may leverage the existing functionality of a port controller 530 to detect an electrically conductive liquid within the port 250. The port controller 530 may be configured to control the voltage levels at the electrical contacts 330 of the port 250 as part of its responsibilities for providing connectivity at the port 250. The monitor module 310 may use the hardware and firmware configuration of the port controller 530 to maintain a voltage on a pin of the port 250, and to detect a short circuit between two or more pins of the port 250.

For example, the monitor module 310 may maintain 5 Volts on the $V_{Bus}$ pin of the port 250. In another embodiment, the monitor module 310 maintains 3.3 Volts on the D+ or D− pin of the port 250. The monitor module 310 may further use existing port controller 530 hardware and/or firmware to monitor the appropriate pins for changes in properties in order to detect exposure to an electrically conductive liquid.

Certain aspects of the moisture detector 120 may be implemented in other components of the electronic device 110. For example, the instruction module 418 may be implemented as part of the operating system of the electronic device 110. The protection module 414 may be implemented, at least in part, in cooperation with the BIOS 520 in order to cause the electronic device 110 to boot into a safe mode. Those of skill in the art will appreciate that the modules described above may be implemented on various devices, and at various levels, of the electronic device 110.

Figure 6:
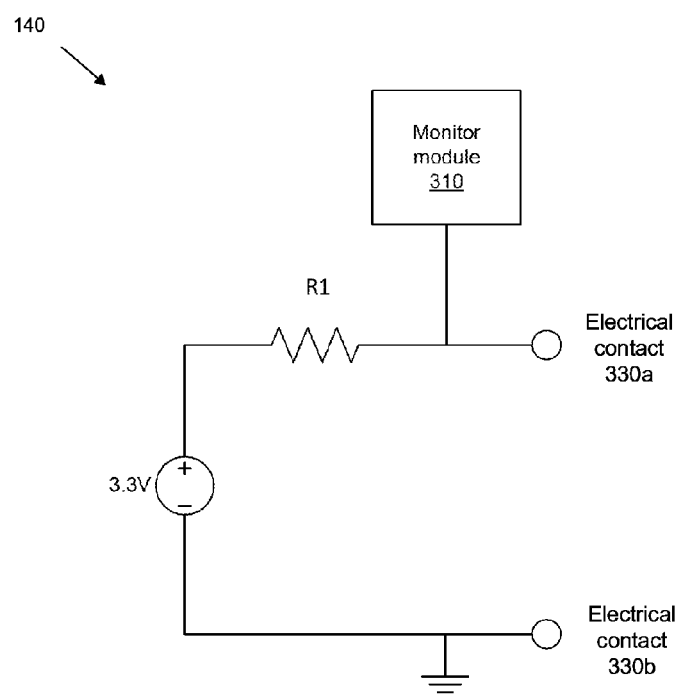
FIG. 6 is a circuit schematic illustrating an embodiment of a moisture detection circuit.

FIG. 6 represents a simplified circuit schematic representative of a moisture detection circuit 140. In the depicted embodiment, the moisture detection circuit 140 incorporates electrical contact 330a and electrical contact 330b of the port 250. The electrical contacts 330a and 330b may be exposed on an exterior face of the electronic device 110. The electrical contacts 330a and 330b are typically exposed in order to provide the necessary connection for the port 250. The hardware implementing the logic and sensing functions of the monitor module 310 may be situated in an interior of the electronic device 110.

FIG. 6 illustrates a voltage source providing 3.3 Volts for the moisture detection circuit 140. The port controller 530 may be the voltage source for the moisture detection circuit 140. For example, the voltage source may be a pin of an integrated circuit hosting the port controller 530 (FIG. 5). The port controller 530 may include a separate pin providing the electrical ground shown in FIG. 6. The monitor module 310 may maintain the 3.3 Volts for the moisture detection circuit 140.

The moisture detection circuit 140 may include a resistor R1. R1 may, in certain implementations, be a resistor, or it may represent the resistance in the path between the voltage source and the electrical contact 330a. The monitor module 310 may measure the voltage at the electrical contact 330a, as shown in FIG. 6. The monitor module 310 may also monitor the current at the electrical contact 330a. The monitor module 310 may measure voltage and/or current at a different location than that shown in FIG. 6.

When the port 250 is not connected, there is no connection between the electrical contact 330a and the electrical contact 330b. As a result, no current flows through R1 and the voltage difference between the electrical contact 330a and electrical contact 330b will be 3.3 Volts. The monitor module 310 may detect when a device is connected to the port 250 and cease monitoring the voltage and/or current for purposes of determining whether the electronic device 110 is exposed to an electrically conductive liquid while the port 250 is in the connected state.

In the event that the electronic device 110 is exposed to an electrically conductive liquid, the electrically conductive liquid may short circuit the moisture detection circuit 140 by forming an electrically conductive path between the electrical contact 330a and the electrical contact 330b. As a result, current flows through the resistor R1, causing voltage to drop over R1, and changing the voltage at the electrical contact 330a. The monitor module 310 may detect the changes in the voltage and/or the current through the moisture detection circuit 140 as a result of the electrically conductive liquid forming a path between the electrical contacts 330a and 330b. When the electronic device 110 is removed from the electrically conductive liquid and the electrically conductive liquid forming the connection between the electrical contacts 330a and 330b is removed, the moisture detection circuit 140 returns to its starting state as described above. The log module 416 (FIG. 4) may log the properties measured by the monitor module 310 during the period of time when there is a short circuit between the electrical contacts 330a and 330b.

The sensor module 312 may receive the measured properties of the moisture detection circuit 140 from the monitor module 310 and may compare the measured properties to reference properties characteristic of exposure to an electrically conductive liquid. As described above, the sensor module 312 may include a plurality of exposure models including reference properties.

The actual moisture detection circuit 140 may be more complicated than the example shown in FIG. 6. For example, where the port 250 is used to implement the moisture detection circuit 140, there may be more than two electrical contacts 330a-b. In addition, there may be more than one voltage source as more than one electrical contact 330 may have a voltage maintained on it while the port 250 is in its unconnected state. In certain embodiments, the monitor module 310 measures properties at more than one location in the moisture detection circuit 140. The monitor module 310 may, for example, monitor the properties at each electrical contact 330 in the port 250. In such embodiments, the monitor module 310 may be configured to monitor for short circuits between an electrical contact 330a with a first voltage and a second electrical contact 330b at ground, between two electrical contacts 330 with non-zero voltages, or combinations thereof.

In certain embodiments, the port 250 may include one or more electrical contacts 330 that do not have an assigned role and that are reserved. In certain embodiments, the monitor module 310 may cause a reference voltage to be placed on a reserved pin in order to provide a reference voltage for determining whether the electronic device 110 has been exposed to an electrically conductive liquid.

Figure 7:
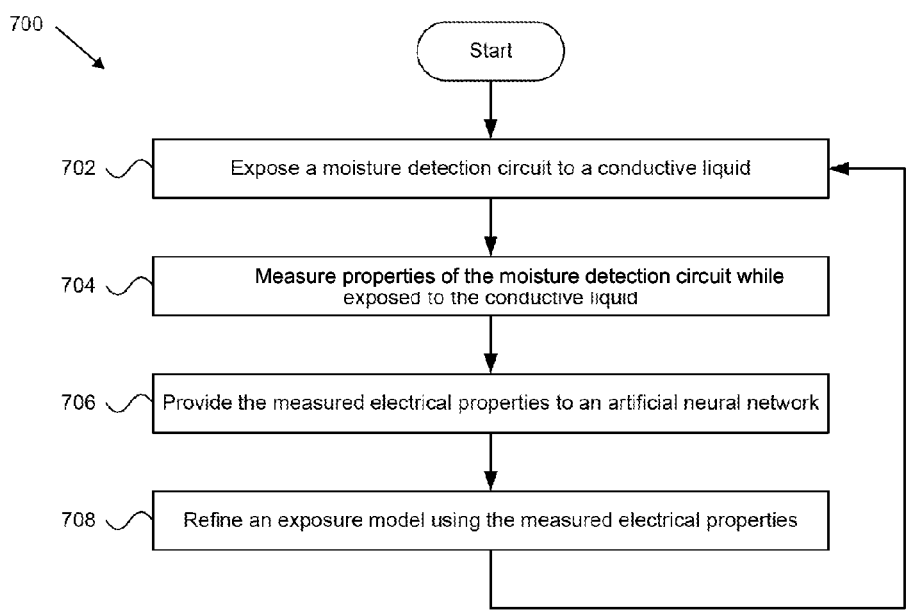
FIG. 7 is a flow chart illustrating an embodiment of a method for creating an exposure model.

FIG. 7 illustrates one embodiment of a method 700 for determining the reference properties characteristic of exposure to an electrically conductive liquid. The method 700 may begin at reference numeral 702 with exposing a moisture detection circuit 140 to an electrically conductive liquid. The method 700 may also include, at reference numeral 704, measuring properties of the moisture detection circuit 140 while the moisture detection circuit 140 is exposed to the electrically conductive liquid.

The method 700 may also involve, at reference numeral 706, providing the measured properties to an artificial neural network (ANN). The ANN may then, at reference numeral 708, refine the exposure model using the measured properties. The method 700 may repeat until the ANN has developed a sufficiently robust exposure model that allows the sensor module 312 (FIG. 3-5) to determine whether the electronic device 110 has been exposed to an electrically conductive liquid.

In certain embodiments, the method 700 is implemented for each of a series of conductive liquids. For example, the method 700 may be executed separately to develop exposure models for tap water, pool water, salt water, and/or other conductive liquids. The sensor module 312 may use one or more of the exposure models to determine whether the electronic device 110 has been exposed to an electrically conductive liquid. In certain embodiments, the exposure models are used to determine threshold values for one or more properties. The sensor module 312 may determine that the electrical device 110 has been exposed to an electrically conductive liquid in response to a property (such as the current level) exceeding the threshold value.

Figure 8:
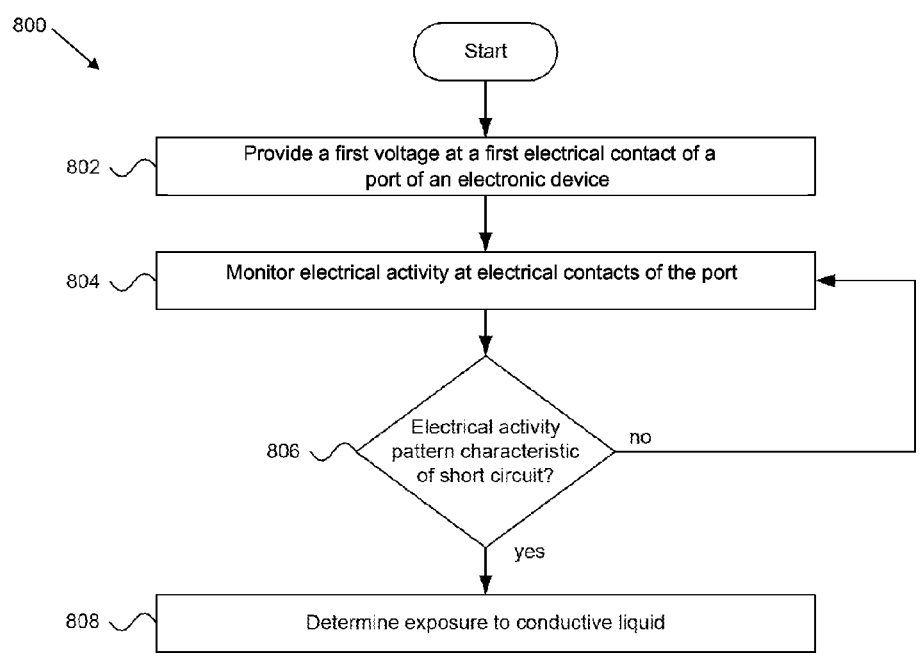
FIG. 8 is a flow chart illustrating an embodiment of a method for detecting exposure of a port or another group of electrical contacts to an electrically conductive liquid.

FIG. 8 illustrates one embodiment of a method 800 for detecting the presence of an electrically conductive liquid in an electronic device 110. The method 800 may begin at reference numeral 802 with providing a first voltage at a first electrical contact 330 of a plurality of electrical contacts 330 in a port 250 of the electronic device 110. In certain embodiments, the monitor module 310 provides the first voltage while the port 250 is in an unconnected state. The method 800 may also involve, at reference numeral 804, the monitor module 310 monitoring the electrical activity at one or more of the electrical contacts 330 of the unconnected port 250.

The monitor module 310 may determine, at reference numeral 806, whether the electrical activity pattern at the electrical contacts 330 is characteristic of a short circuit caused by an electrically conductive liquid. If the monitor module 310 does not sense such an electrical activity pattern, the monitor module 310 may continue to monitor the electrical activity pattern at reference numeral 804. If the monitor module 310 senses a change in the electrical activity pattern, the sensor module 312 may determine, at reference numeral 808, that the electronic device 110 has been exposed to an electrically conductive liquid.

This application makes reference to one or more modules. A module refers to a component for executing one or more functions. A module may be realized as hardware, firmware, software, or a combination thereof. The module may include one or more instructions that are stored in one or more memory locations and that are executable by a processor. These instructions may be stored in the same storage unit, or dispersed across separate storage units. The module may be stored in volatile and/or non-volatile memory. The module may be realized as a computer program product stored on a computer-readable storage medium. The computer-readable storage medium may be any tangible storage medium, volatile and non-volatile, capable of storing a computer program product such as CD, DVD, RAM, ROM, Flash memory, remotely in the "cloud", and others.

Where the module comprises executable instructions, the module may be stored by different components in a computing system and the instructions may be executed by different components within the computing system. For example, a single module may include instructions executable by a general purpose central processing unit (CPU) and instructions executable by a microcontroller within the computing system. Representations of a module as a block within the FIGs of this application are for convenience, and are not meant to imply that the module is a single hardware unit separate from other hardware units in the computing system.

Although the foregoing disclosure provides many specifics, these should not be construed as limiting the scope any of the ensuing claims. Other embodiments may be devised which do not depart from the scopes of the claims. Features from different embodiments may be employed in combination. Accordingly, all additions, deletions and modifications to the disclosed subject matter that fall within the scopes of the claims are to be embraced thereby. The scope of each claim is indicated and limited only by its plain language and the full scope of available legal equivalents to its elements.

What is claimed:

1. An electronic device comprising:
   a plurality of electronic components;
   a port for enabling communication between the electronic device and another device, the port comprising a first electrical contact and a second electrical contact; and
   a moisture detector configured to detect exposure of the port to an electrically conductive liquid, the moisture detector including:
      a monitor module configured to maintain a voltage on the first electrical contact and to detect a short circuit between the first electrical contact and the second electrical contact; and
      a sensor module configured to determine that the port of the electronic device is exposed to an electrically conductive liquid in response to the monitor module detecting the short circuit.

2. The electronic device of claim 1, wherein:
   the monitor module is further configured to determine a connection state of the port; and
   the sensor module is further configured to determine that the port of the electronic device is exposed to the electrically conductive liquid in response to the monitor module:
      detecting that the port is in an unconnected state; and
      detecting the short circuit.

3. The electronic device of claim 1, further comprising:
   a protection module configured to cause the electronic device to enter a safe mode in response to the sensor module determining that the port of the electronic device is exposed to the electrically conductive liquid.

4. The electronic device of claim 1, further comprising:
   a protection module configured to terminate communication between a power supply and at least some electronic components of the plurality of electronic components.

5. The electronic device of claim 4, wherein the protection module is configured to terminate communication between the power supply and all electronic components other than electronic components of the moisture detector.

6. The electronic device of claim 1, further comprising:
   an alert module configured to generate an alert that the port of the electronic device has been exposed to an electrically conductive liquid.

7. The electronic device of claim 6, wherein the alert module is configured to:
   generate an alarm perceivable by a user of the electronic device; or
   cause a display to visually indicate to the user that the port of the electronic device has been exposed to an electrically conductive liquid.

8. The electronic device of claim 6, wherein the alert module is configured to generate and transmit a message to a remote monitoring service.

9. The electronic device of claim 1, further comprising:
   a log module configured to log instances of the sensor module determining that the port of the electronic device is exposed to the electrically conductive liquid.

10. The electronic device of claim 1, further comprising:
    an instruction module configured to provide a user with one or more instructions for treating the electronic device following exposure of the port to the electrically conductive liquid.

11. The electronic device of claim 1, further comprising:
    a confirmation module configured to request user confirmation that the port of the electronic device was exposed to the electrically conductive liquid.

12. The electronic device of claim 1, further comprising:
    a moisture-resistant coating on at least one electronic component within an interior of the electronic device.

13. The electronic device of claim 1, wherein the port is a USB port, a proprietary port or a receptacle for an audio jack.

14. The electronic device of claim 1, wherein the moisture detector is implemented in a controller for the port.

15. The electronic device of claim 1, wherein the first electrical contact is a power electrical contact and the second electrical contact is a ground electrical contact.

16. A moisture detector, comprising:
a monitor module configured to monitor one or more properties of a moisture detection circuit, the moisture detection circuit comprising a first node having a first voltage and a second node having a second voltage, the second voltage being different from the first voltage;
a sensor module configured, in response to a predetermined variation in the one or more properties of the moisture detection circuit from reference properties characteristic of exposure of at least one of the first node and the second node of the moisture detection circuit to an electrically conductive liquid, to determine that at least one of the first node and the second node of the moisture detection circuit is exposed to the electrically conductive liquid; and
a log module configured to create a log entry comprising the properties of the moisture detection circuit causing the sensor module to determine that at least one of the first node and the second node of the moisture detection circuit was exposed to the electrically conductive liquid.

17. The moisture detector of claim 16, wherein a port of an electronic device comprises the moisture detection circuit.

18. The moisture detector of claim 16, wherein the one or more properties of the moisture detection circuit comprise:
a current in the moisture detection circuit;
a voltage in the moisture detection circuit;
a resistance in the moisture detection circuit; or
a frequency in the moisture detection circuit.

19. The moisture detector of claim 16, wherein the sensor module determines that at least one of the first node and the second node of the moisture detection circuit of the electronic device is exposed to the electrically conductive liquid in response to the one or more properties of the moisture detection circuit corresponding to the reference properties characteristic of a short circuit.

20. The moisture detector of claim 16, wherein the reference properties characteristic of exposure to the electrically conductive liquid are generated using a learning algorithm or system.

21. The moisture detector of claim 16, further comprising:
the moisture detection circuit, with the first node and the second node being at least partially exposed to an exterior of an electronic device of which the moisture detector is a part.

22. The moisture detector of claim 16, further comprising:
a protection module configured to terminate power to an electronic device in response to the sensor module determining that at least one of the first node and the second node of the moisture detection circuit is exposed to the electrically conductive liquid.

23. The moisture detector of claim 22, wherein the protection module is further configured to cause an electronic device to power on in a safe mode in response to a user powering on the electronic device after the sensor module determines that the at least one of the first node and the second node of the moisture detection circuit is exposed to the electrically conductive liquid.

24. The moisture detector of claim 16, further comprising:
a confirmation module configured to receive user confirmation that at least one of the first node and the second node of the moisture detection circuit was exposed to the electrically conductive liquid.

25. A method for detecting exposure of a group of electrical contacts of an electronic device to moisture, comprising:
providing a first voltage to a first electrical contact of a plurality of electrical contacts in a port of an electronic device while the port is in an unconnected state;
monitoring electrical activity at one or more electrical contacts of the plurality of electrical contacts while the port is in the unconnected state;
sensing an electrical activity pattern at the one or more electrical contacts that is characteristic of a short circuit caused by an electrically conductive liquid; and
determining exposure of one or more of the plurality of electrical contacts to the electrically conductive liquid in response to sensing the electrical activity pattern that is characteristic of the short circuit caused by the electrically conductive liquid.

26. The method of claim 5, further comprising:
powering down one or more components of the electronic device in response to determining exposure of the one or more electrical contacts to the electrically conductive liquid.

27. The method of claim 25, further comprising:
creating an exposure model from electrical activity patterns of test electronic devices with one or more electrical contacts exposed to the electrically conductive liquid.

28. The method of claim 27, wherein determining exposure of the one or more of the plurality of electrical contacts to the electrically conductive liquid comprises determining that the electrical activity pattern matches the exposure model.

29. The method of claim 27, further comprising:
creating the exposure model with a learning algorithm or system.

30. A moisture detector, comprising:
a monitor module configured to monitor one or more properties of a moisture detection circuit, the moisture detection circuit comprising a first node having a first voltage and a second node having a second voltage, the second voltage being different from the first voltage;
a sensor module configured, in response to a predetermined variation in the one or more properties of the moisture detection circuit from reference properties characteristic of exposure of at least one of the first node and the second node of the moisture detection circuit to an electrically conductive liquid, to determine that at least one of the first node and the second node of the moisture detection circuit is exposed to the electrically conductive liquid; and
a confirmation module configured to receive user confirmation that at least one of the first node and the second node of the moisture detection circuit was exposed to the electrically conductive liquid.

* * * * *